US007010982B2

(12) United States Patent
Bergman

(10) Patent No.: US 7,010,982 B2
(45) Date of Patent: Mar. 14, 2006

(54) METHOD OF ULTRASONICALLY INSPECTING AIRFOILS

(75) Inventor: Robert William Bergman, Scotia, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/834,854

(22) Filed: Apr. 30, 2004

(65) Prior Publication Data
US 2005/0241397 A1 Nov. 3, 2005

(51) Int. Cl.
G10N 9/24 (2006.01)
(52) U.S. Cl. .............................. 73/618; 73/625; 73/583
(58) Field of Classification Search .................. 73/583, 73/596, 600, 602, 620, 626, 618, 622, 625
See application file for complete search history.

(56) References Cited

U.S. PATENT DOCUMENTS

| 4,817,433 | A | * | 4/1989 | Sato ............................ 73/620 |
| 5,798,461 | A | * | 8/1998 | Banta et al. ................... 73/625 |
| 6,382,028 | B1 | * | 5/2002 | Wooh et al. ................... 73/602 |
| 6,789,427 | B1 | * | 9/2004 | Batzinger et al. ............. 73/614 |
| 6,813,950 | B1 | * | 11/2004 | Glascock et al. ............. 73/633 |

* cited by examiner

Primary Examiner—Helen Kwok
(74) Attorney, Agent, or Firm—Nixon & Vanderhye P.C.

(57) ABSTRACT

A method is disclosed for nondestructively examining airfoils for defects without removing them from the turbine machines of which they are a part. The method uses phased array ultrasound technology, which can be used with all types of airfoils. The angle of entry of the ultrasonic beam is varied by using phased array ultrasound technology. The phased array ultrasound allows an inspector to steer the ultrasonic beam toward an area of interest within the airfoil. The phased array allows an inspector to monitor multiple angles at once. So long as the scan angle does not exceed a calibrated range, an inspector can monitor an area of interest, no matter what the sound beam entry surface angle is. The ultrasonic beam is steered or phased to inspect different orientations with one scan. The method uses a phased array transducer that is a linear array probe that is comprised of a series of transducers. Each of these transducers is programmed to trigger at predetermined time intervals and also receive at predetermined time intervals. The signals acquired by each transducer are then processed by a computer to give a composite view of a tested region so that a defect indication can be viewed.

26 Claims, 2 Drawing Sheets

METHOD OF ULTRASONICALLY INSPECTING AIRFOILS

The present invention relates to a method for nondestructively examining for defects in machine components, such as airfoils, and in particular, to a method of nondestructively examining such components for defects using phased array ultrasound technology.

BACKGROUND OF THE INVENTION

With the development of modern, more complex aerodynamic power generation machines, there has been an increased amount of study into the inspection of machine components to develop methods of inspecting such components for defects in non-invasive ways. Some of the most critical components of the machines are in locations that allow limited access to them. Most studies to date have used visual, radiographic, liquid penetrant and eddy current nondestructive methods of inspection. To perform visual, liquid penetrant and eddy current tests, it is necessary to have access to all surfaces of the machine component being tested. For many machine components, this is not possible without at least some disassembly of the machine.

To perform a radiographic exam, a piece of radiographic film must be placed on the opposite side of the machine component being examined using the radiation source. There must also be a minimal amount of material between the radiation source and the component being tested. In a fully assembled machine, it is often not possible to accomplish either of these tasks.

Traditionally, the use of ultrasound to test machine airfoils for defects has been limited due to the thin and complex geometries of airfoils in general. The largest problem with using ultrasound to test airfoils is that the surfaces of an airfoil from which a test can be done constantly changes in angle with respect to the area of interest in the airfoil. To perform an inspection of a changing surface using ultrasound, the use of many discrete transducers at a variety of angles would be required. As such, the use of a single transducer would be impractical and unreliable.

U.S. Pat. No. 6,082,198, discloses the use of phased array ultrasound to inspect for defects from a surface which is at a constant angle to the area to be inspected. The disclosed method inspects from the hub, and relies on a constant access of symmetry. It cannot be used with parts which are contained in a machine due to the need for access to a beam entry surface that is blocked by other components.

Airfoils are a highly stressed component of aerodynamic machines. Because of these high stresses, an airfoil should be inspected regularly for defects. To perform non-destructive tests on airfoils, the machines which contain these parts must be disassembled to some extent to gain access to the entire airfoil. This disassembly is costly and time-consuming. To reduce the time and cost involved with the disassembling of a machine, a non-destructive technique is needed which will not be affected by a continual change in geometry over the entire airfoil surface.

BRIEF DESCRIPTION OF THE INVENTION

In an exemplary embodiment of the invention, a method of nondestructively inspecting a machine component for defects using a phased array ultrasonic beam, the method comprises the steps of identifying an area of interest in the component where at least one defect is expected to be located, determining a range of angles for steering the phased array ultrasonic beam to the area of interest, and thereby keeping the area of interest in view relative to a scan of the ultrasonic beam across a sector of a surface of the component where the ultrasonic beam is caused to enter the component, and conducting the sector scan whereby phased array ultrasonic beam signals are caused to enter the component and then re-acquired and processed to provide a composite view of the area of interest so that a defect indication can be viewed, the entire area of interest being monitored without interruption of the scan.

In another exemplary embodiment of the invention, a method for nondestructively inspecting airfoils for defects comprises the steps of identifying an area of interest in the component where at least one defect is expected to be located, determining a range of angles for steering the phased array ultrasonic beam to the area of interest, and thereby keeping the area of interest in view relative to a scan of the ultrasonic beam across a sector of a surface of the component where the ultrasonic beam is caused to enter the component, and conducting the sector scan whereby phased array ultrasonic beam signals are caused to enter the component and then re-acquired and processed to provide a composite view of the area of interest so that a defect indication can be viewed, the entire area of interest being monitored without interruption of the scan.

In yet another exemplary embodiment of the invention, a method of nondestructively inspecting an airfoil for defects using a transducer probe emitting a phased array ultrasonic beam comprises the steps of identifying an area of interest in the airfoil where at least one defect is expected to be located, selecting the transducer probe according to the size of the expected defect and to where the area of interest in the airfoil is expected to be located, determining a beam angle of incidence and a range of angles for steering the phased array ultrasonic beam to the area of interest to thereby keep the area of interest in view relative to a sweep of the transducer probe across a sector of a surface of the airfoil where the ultrasonic beam is caused to enter the airfoil, conducting a sweep of the transducer probe across the sector of the airfoil surface, whereby phased array ultrasonic beam signals are emitted from the transducer probe so as to enter the airfoil and then re-acquired by the transducer probe, and processing the re-acquired ultrasonic beam signals using a computer and stacking the signals to provide a composite view of the area of interest in the airfoil where the defect is expected to be located.

BRIEF DESCRIPTION OF THE DRAWINGS

The advantages of the present invention will be more completely understood and appreciated by careful study of the following more detailed description of the presently-preferred exemplary embodiment of the invention taken in conjunction with the accompanying drawings, in which.

DETAILED DESCRIPTION OF THE INVENTION

The present invention is directed to a method of nondestructively examining machine components, such as airfoils, for defects without removing the components from the machines of which they are a part. The method of the present invention uses well-known phased array ultrasound technology to nondestructively examine the components for defects, and is applicable to all types of components, in that it can be used to test any geometry where the surface of the component through which the ultrasonic sound beam enters changes in angle with respect to the part of the component to be examined for defects.

The method of the present invention is applicable to both longitudinal wave and shear wave techniques used to test components without removal of them from the machine containing them. The angle at which the ultrasonic beam enters a component to be examined is varied by the transducer probe emitting the beam. The phased array ultrasound allows an inspector to steer the ultrasonic beam toward an area of interest in a component where defects are likely to be found. The phased array ultrasound also allows the inspector to monitor multiple angles at once. So long as the angle does not exceed a calibrated range, an inspector can monitor the area of interest, no matter what the sound beam entry surface angle is.

Figure 1:
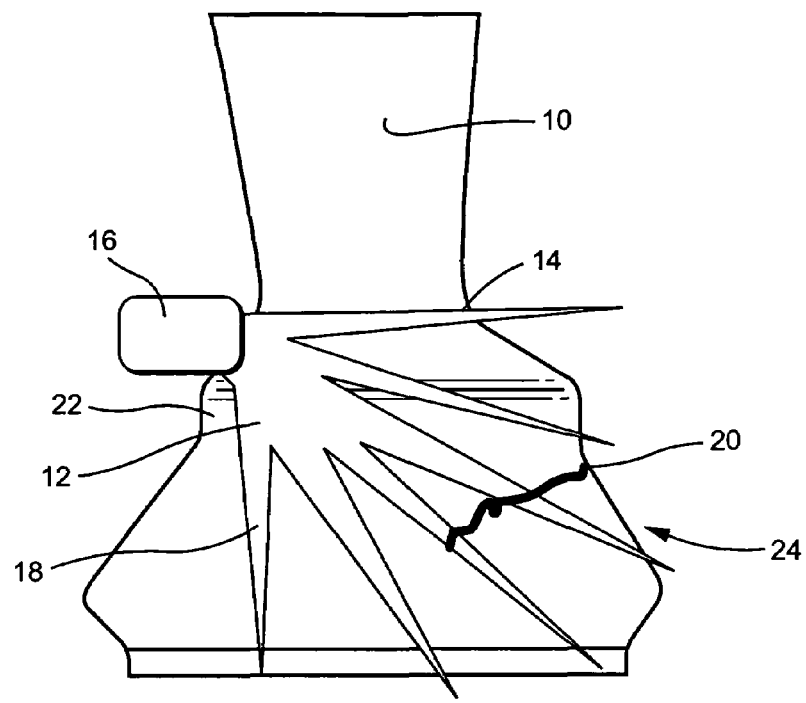
FIG. 1 is a schematic diagram illustrating the method of the present invention for nondestructively examining airfoils for defects using phased array ultrasound.

Referring to FIG. 1, the present invention solves the problem of nondestructively testing the complex geometries of machine components, such as an airfoil 10 shown in FIG. 1, by "steering" or "phasing" an ultrasonic beam 12 (phased array ultrasound) to inspect airfoil 10 for defects using different orientations with one scan. As can be seen in FIG. 1, the horizontal line 14 of beam 12 represents a sound path normal to or directly below a transducer probe 16. The vertical line 18 of beam 12 represents 90 degrees of beam steering or "phasing". The cracked line 20 shown in airfoil 10 indicates a defect in the airfoil. As can be seen from FIG. 1, defect 20 can only be seen if the operator using probe 16 is using a 45° to 50° beam angle relative to the normal beam 14. As the surface 22 where transducer 16 is in contact with airfoil 10 changes its orientation, the angle at which beam 12 enters airfoil 10 changes, so that the angle of beam 12 to scan the area of interest 24 in airfoil 10 will change accordingly.

The phased array transducer probe 16 used with the method of the present invention is a linear array probe which is comprised of a series of transducers. Each of these transducers is triggered at predetermined time intervals and receives an ultrasound signal back at predetermined time intervals. This predetermined triggering and receiving is the phasing which allows the steering of beam 12. The ultrasound signals acquired by each transducer is then processed by a computer to give a composite view of the area of interest 24 that is being examined.

Figure 2:
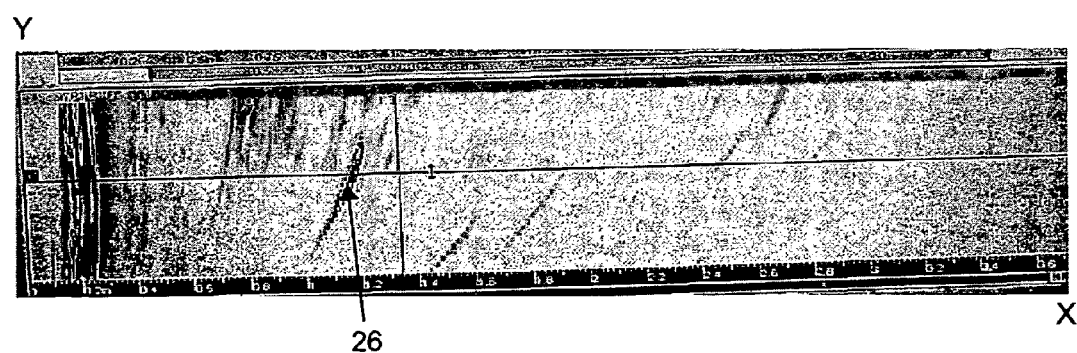
FIG. 2 is a graph showing a view of a defect indicated in an airfoil using the method of the present invention for nondestructively examining the airfoil using phased array ultrasound.

To inspect an airfoil 10 from its blade surface 22, the range of angles which are needed to keep the area of interest 24 in view must first be determined. A sector scan or sweep is then set up which is comprised of the angles required for inspection of the area of interest. During inspection, the entire area of interest 24 can be monitored without interruption of the test. Also, by using an ultrasonic phased array sector scan, parts in a machine with limited access, such as airfoils, can be readily inspected without disassembling the machine containing the airfoil. This is because the inspection method of the present invention does not require access to all areas of interest by physical means. By using a phased array beam, an operator can see all beam angles of interest in one scan. This allows for a more comprehensive view of the inspection area 24 and reduces the test variation. FIG. 2 shows a view of a defect indication 26 noted using the inspection method of the present invention with phased array technology. The "Y" axis represents the ultrasonic sound beam angle and the "X" axis represents the ultrasonic sound beam travel.

The inspection method of the present invention enables the inspection of an airfoil 10 by using the blade or vane surface 22 as the beam entry surface. The range of angles which are needed to keep an area of interest in view during a scan is preferably determined using a drawing of the part 10 to be inspected. Assuming that the ultrasonic sound beam enters airfoil 10 at a particular location on the blade or vane surface 22 of airfoil 10, a protractor can be used with the drawing of the airfoil to determine the beam angle as to where a defect is expected to be and the range of angles needed to steer the ultrasonic beam 12 to keep the area of interest 24 in view during a scan. By using the protractor, the angle to where a defect is likely to be located, i.e., the angle at which the beam should be refracted, can be determined relative to the entry surface of the airfoil. Using Snells Law, the angle of refraction of the ultrasonic sound signals entering a part to be inspected can be determined from the angle of incidence at which the ultrasonic sound enters the part. That is, the ratio of the sine of the incident angle of the ultrasonic sound to the sine of the refracted angle of the ultrasonic sound is constant. Given the geometry of a part to be inspected and the angle to the area likely to contain the defect, the scan angle can be readily determined. Yet another way to determine the test angle is to use a series of discretely angled transducers. A map of the test area can be made by finding which angles produce the optimal test at each area of the test surface.

Using a drawing of a part 10 to be inspected allows the angle to the area 24 to be inspected to be readily determined. For example, if a defect is positioned at 15° from a perpendicular to the entry surface of an airfoil to be inspected, a scan angle of 10°–40° might be used so that the area of interest 24 is always inside the field of view of an inspector inspecting part 10. If the defect is positioned at an angle of 30°, a scan angle of 20°–40° might be used.

The scan angle will change if the material from which the part 10 to be is made changes. The scan angle for a part made of steel will be different from the scan angle for the same part made of aluminum because the velocity at which sound travels within the two materials will vary. Velocity is part of the calculation of the scan angle, which will change, depending on the material used to make the airfoil to be inspected. Using Snells Law, the angle of refraction of the ultrasonic sound signals entering a part to be inspected can be determined from the angle of incidence at which the ultrasonic sound enters the part. That is, the ratio of the sine of the incident angle of the ultrasonic sound to the sine of the refracted angle of the ultrasonic sound is equal to the velocity of the ultrasonic sound in the incident material divided by the velocity of the ultrasonic sound in the refracted material. Thus, depending on the density of the material, the scan or sweep angle is going to change.

The scan or sweep angle, which can be considered to be a window, is constant, but the angle of the window is not always going to be constant. Because the surface through which the ultrasonic beam enters a component part is changing in angle, a single scan or sweep can be used because of the present invention's use of a phased array ultrasonic beam. Without a phased array ultrasonic beam, 20 or 30 exams on the same part to be inspected may be necessary, depending on the amount of change in the angle of the entry surface over which the sweep is made using a transducer probe 16.

The inspection method of the present invention allows data relating to defect 20 that is gathered during an inspection to be digitized and saved so that successive inspections can be compared to one another with greater reliability, thereby allowing variations between inspectors to be greatly reduced. The ability to characterize flaws is another advantage of the inspection method of the present invention. When the ultrasonic beam entry surface 22 changes orientation, direct measurement of flaw sizes becomes difficult. To address this issue, samples can be made with known size defects (or reflectors). Measurements are taken of these reflectors at each location where the entry angle changes by ±3 degrees. The reflector sizes are documented for further reference. If a suspected reflector is found during an inspection at a certain ultrasound path surface entry angle, it is compared to the reference reflector. The square of the ratio of the test reflector to the reference reflector is used to derive the defect size from the known reflector size. The length of the defect can also be determined due to the fact that the defect indication can be seen for its entire length with a single phased array ultrasound scan.

The preferred probe used with the inspection method of the present invention includes a plurality of transducers lying in a line and numbered 1 through 16. Positive steering of the ultrasonic beam occurs as the transducers are triggered 1, 2, 3, etc. up through 16, so that the beam is tipped up toward where transducer 16 is positioned. Negative steering of the ultrasonic beam occurs as the transducers are triggered 16, 15, 14, etc. down through 1, so that the beam is tipped down toward where transducer 1 is positioned. Steering of the ultrasonic beam also occurs as a result of each emitted wave front interfering with the emitted wave front that preceded it.

As part of the inspection method of the present invention, transducer probe size and frequency must be determined. Phased array probes can be manufactured in a wide variety of sizes and frequencies. A probe can be designed for most any application and can be made small enough to fit into most spaces. The number of transducer chips included in the probe used with the method of the present invention to apply the ultrasonic beam will vary according to the size of the probe. Typically, the size of the probe is selected according to the size of the expected defect and where in the part to be inspected the defect is expected to be located.

Using phased array ultrasound with a machine component, such as airfoil 10, allows the airfoil to be inspected with minimal disassembly of the machine in which it is located. Transducer probe 16 can be fitted to a manipulating device to gain access to inspection areas not accessible by other means of inspection without some form of machine tear down. Many defects which form in areas of machine components that are inaccessible in a fully assembled machine can be detected using the nondestructive inspection method of the present invention.

Figure 3:
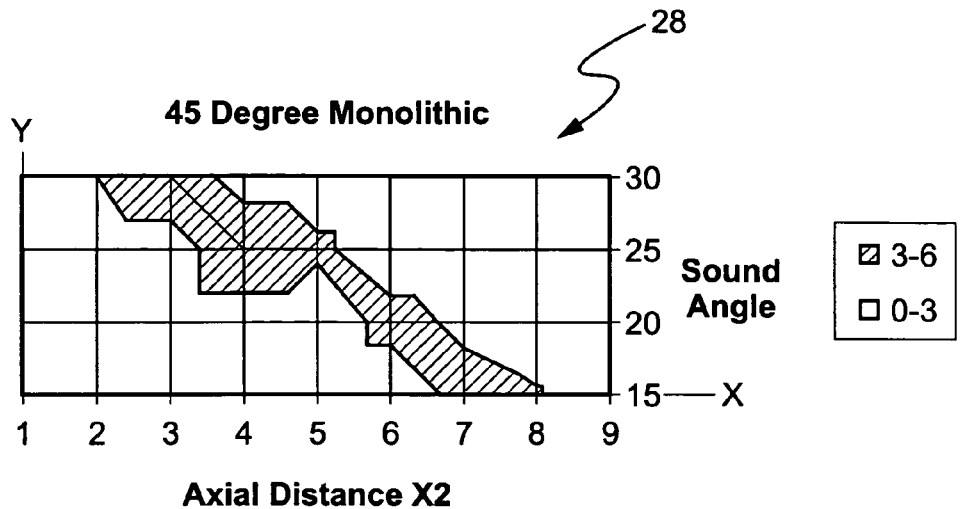
FIG. 3 is a graph showing a response surface using conventional ultrasound to examine a blade that has been notched and cracked.
Figure 4:
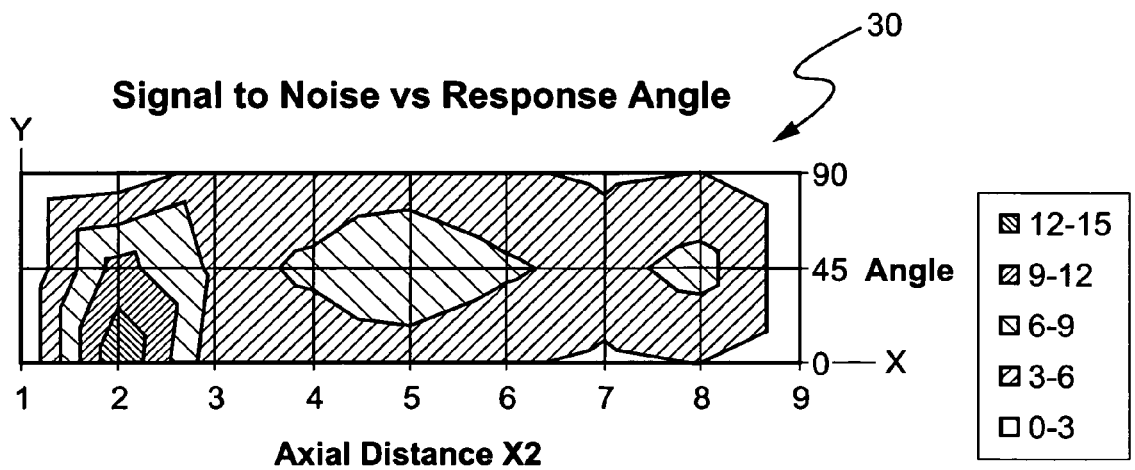
FIG. 4 is a graph showing a response surface using phased array ultrasound to examine a blade that has been notched and cracked.

The reliability of inspections using phased array ultrasound is evidenced by the data shown in FIGS. 3 and 4 herein. The phased array ultrasonic responses from airfoil blades that were notched and cracked were compared with responses using conventional ultrasound to demonstrate the capability of phased array ultrasound for testing parts. FIG. 3 shows a response surface using conventional ultrasound. FIG. 4 shows a response surface using phased array ultrasound. These response surfaces represent the signals seen at various orientations of an airfoil. The "X" axis is the distance along a sound beam entry surface which is changing in angle. The "Y" axis is the angle between the sound entry surface and the area of interest. The shading maps 28 and 30 represent signal to noise ratios. From FIGS. 3 and 4, the probability of detection of an ultrasound signal representing a defect 20 can be seen. The shading maps 28 and 30 of FIGS. 3 and 4 show that the signals of defects are much more easily seen using phased array ultrasound (FIG. 4) rather than conventional ultrasound (FIG. 3). It should also be noted that each beam angle represented in FIG. 3 is done with a different transducer. This introduces interruption in the scans. The beam angles represented in FIG. 4 for phased array ultrasound are done with a single transducer probe scan.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of nondestructively inspecting a machine component for defects using a phased array ultrasonic beam, the method comprising the steps of:

identifying an area of interest in the component where at least one defect is expected to be located, providing a transducer probe for emitting the phased array ultrasonic beam, determining a range of angles relative to an angle of incidence at which the transducer probe emits the ultrasonic beam into the component for steering the phased array ultrasonic beam to the area of interest, and thereby keeping the area of interest in view relative to a scan of the transducer probe and thus ultrasonic beam across a sector of a surface of the component where the ultrasonic beam is caused to enter the component, and conducting the sector scan by scanning the transducer probe across the sector surface while the probe is in contact with the sector surface, whereby phased array ultrasonic beam signals emitted from the transducer probe are caused to enter the component at an angle of incidence that changes as the sector surface contacted by the transducer probe changes orientation and then re-acquired and processed to provide a composite view of the area of interest so that a defect indication can be viewed, an entire area of interest being monitored without interruption of the scan.

2. The method of claim 1, wherein the transducer probe is a linear array probe which is comprised of a series of transducers.

3. The method of claim 2, wherein each of the transducers is triggered at one of a plurality of first predetermined time intervals and receives at one of a plurality of second predetermined time intervals.

4. The method of claim 3, wherein the ultrasonic beam signals are re-acquired by each transducer and then processed by a computer and stacked to give a composite view of the area of interest so that the defect can be viewed.

5. The method of claim 1, wherein the range of angles for steering the phased array ultrasonic beam is determined using a drawing of the component and a protractor to measure an angle of refraction from the surface of the component where the ultrasonic beam is caused to enter the component and the area of interest in the component where the defect is expected to be located.

6. The method of claim 5, wherein the angle of refraction for the ultrasonic beam after the beam enters the component varies with changes in the angle of incidence for the ultrasonic beam entering the surface of the component.

7. The method of claim 6, wherein the range of angles for steering the phased array ultrasonic beam is approximately ±10° around the ultrasonic beam's angle of incidence.

8. The method of claim 1 further comprising comparing a test defect reflector with at least one documented reflector made with known size defects to determine a size of a test defect in the component.

9. The method of claim 8, wherein the size of the defect in the component is determined from the square of a ratio of the test reflector to a documented reflector.

10. The method of claim 1, wherein the component is examined without removing the component from a machine in which the component is located.

11. A method of nondestructively inspecting an airfoil for defects using a phased array ultrasonic beam, the method comprising the steps of:
identifying an area of interest in the airfoil where at least one defect is expected to be located,
providing a transducer probe for emitting the phased array ultrasonic beam,
determining a range of angles relative to an angle of incidence at which the transducer probe emits the ultrasonic beam into the airfoil for steering the phased array ultrasonic beam to the area of interest, and thereby keeping the area of interest in view relative to a scan of the transducer probe and thus ultrasonic beam across a sector of a surface of the airfoil where the ultrasonic beam is caused to enter the airfoil, and
conducting the sector scan by scanning the transducer probe across the sector surface while the probe is in contact with the sector surface, whereby phased array ultrasonic beam signals emitted from the transducer probe are caused to enter the airfoil at an angle of incidence that changes as the sector surface contacted by the transducer probe changes orientation and then re-acquired and processed to provide a composite view of the area of interest so that a defect indication can be viewed, an entire area of interest being monitored without interruption of the scan.

12. The method of claim 11, wherein the transducer is a linear array probe which is comprised of a series of transducers.

13. The method of claim 12, wherein each of the transducers is triggered at one of a plurality of first predetermined time intervals and receives at one of a plurality of second predetermined time intervals.

14. The method of claim 13, wherein the ultrasonic beam signals are re-acquired by each transducer and then processed by a computer and stacked to give a composite view of the area of interest so that the defect can be viewed.

15. The method of claim 11, wherein the range of angles for steering the phased array ultrasonic beam is determined using a drawing of the airfoil and a protractor to measure an angle of refraction from the surface of the airfoil where the ultrasonic beam is caused to enter the airfoil and the area of interest in the airfoil where the defect is expected to be located.

16. The method of claim 15, wherein the angle of refraction for the ultrasonic beam after the beam enters the component varies with changes in the angle of incidence for the ultrasonic beam entering the surface of the airfoil.

17. The method of claim 16, wherein the range of angles for steering the phased array ultrasonic beam is approximately ±10° around the ultrasonic beam's angle of incidence.

18. The method of claim 11 further comprising comparing a test defect reflector with at least one documented reflector made with known size defects to determine a size of a test defect in the airfoil.

19. The method of claim 18, wherein the size of the defect in the airfoil is determined from the square of a ratio of the test reflector to a documented reflector.

20. The method of claim 11, wherein the airfoil is examined without removing the airfoil from a machine in which the airfoil is located.

21. The method of claim 15 further comprising determining a beam angle for steering the phased array ultrasonic beam using the drawing of the airfoil and the protractor.

22. A method of nondestructively inspecting an airfoil for defects using a transducer probe emitting a phased array ultrasonic beam, the method comprising the steps of:
identifying an area of interest in the airfoil where at least one defect is expected to be located,
providing a transducer probe for emitting the phased array ultrasonic beam,
selecting the transducer probe according to a size of the expected defect and to where the area of interest in the airfoil is expected to be located,
determining a range of angles relative to an angle of incidence at which the transducer probe emits the ultrasonic beam into the airfoil for steering the phased array ultrasonic beam to the area of interest to thereby keep the area of interest in view relative to a sweep of the transducer probe across a sector of a surface of the airfoil where the ultrasonic beam is caused to enter the airfoil,
conducting a sweep of the transducer probe across the sector of the airfoil surface while keeping the probe in contact with the sector surface, whereby phased array ultrasonic beam signals are emitted from the transducer probe so as to enter the airfoil at an angle of incidence that changes as the sector surface contacted by the transducer probe changes orientation and then re-acquired by the transducer probe, and
processing the reacquired ultrasonic beam signals using a computer and stacking the signals to provide a composite view of the area of interest in the airfoil where the defect is expected to be located.

23. The method of claim 22, wherein the transducer probe is a linear array probe which is comprised of a series of transducers.

24. The method of claim 23, wherein the transducers are triggered at one of a plurality of first predetermined time intervals and receive at one of a plurality of second predetermined time intervals.

25. The method of claim 22, wherein the airfoil is examined without removing the airfoil from a machine in which the airfoil is located.

26. The method of claim 22, wherein the beam angle of incidence and range of angles for steering the phased array ultrasonic beam are determined using a drawing of the airfoil and a protractor to measure an angle of refraction from the surface of the airfoil where the ultrasonic beam is caused to enter the airfoil and to the area of interest in the airfoil where the defect is expected to be located.

* * * * *